United States Patent
Dumoulin et al.

(10) Patent No.: US 6,246,896 B1
(45) Date of Patent: *Jun. 12, 2001

(54) MRI GUIDED ABLATION SYSTEM

(75) Inventors: Charles Lucian Dumoulin, London (GB); Robert David Darrow, Scotia, NY (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/198,632

(22) Filed: Nov. 24, 1998

(51) Int. Cl.[7] ................................................. A61B 5/05
(52) U.S. Cl. ........................ 600/411; 600/412; 607/115; 606/34; 606/134
(58) Field of Search .................. 600/412, 411; 607/115; 606/134, 34; 128/653.2

(56) References Cited

U.S. PATENT DOCUMENTS

| | | | |
|---|---|---|---|
| 4,830,012 | 5/1989 | Riederer | 128/653 |
| 5,271,400 | * 12/1993 | Dumoulin et al. | 128/653.2 |
| 5,284,144 | * 2/1994 | Delannoy et al. | 128/653.2 |
| 5,307,808 | * 5/1994 | Dumoulin et al. | 128/653.2 |
| 5,307,812 | 5/1994 | Hardy et al. | 128/653.2 |
| 5,318,025 | * 6/1994 | Dumoulin et al. | 128/653.2 |
| 5,353,795 | 10/1994 | Souza et al. | 128/653.2 |
| 5,433,198 | 7/1995 | Desai | 128/642 |
| 5,437,277 | 8/1995 | Dumoulin et al. | 128/653.1 |
| 5,443,489 | * 8/1995 | Ben-Haim | 607/115 |
| 5,551,426 | 9/1996 | Hummel et al. | 128/642 |
| 5,617,857 | 4/1997 | Chader et al. | 128/653.1 |
| 5,622,170 | 4/1997 | Schulz | 128/653.1 |
| 5,697,925 | 12/1997 | Taylor | 606/34 |
| 5,706,810 | * 1/1998 | Rubinsky et al. | 600/412 |
| 5,711,300 | * 1/1998 | Schneider et al. | 600/412 |
| 5,715,822 | * 2/1998 | Watkins et al. | 600/422 |
| 5,715,882 | 2/1998 | Watkins et al. | 600/422 |
| 5,718,701 | 2/1998 | Shai et al. | 606/41 |
| 5,800,428 | 9/1998 | Nelson et al. | 606/41 |
| 5,910,820 | * 6/1999 | Herz et al. | 348/446 |
| 6,016,439 | * 1/2000 | Acker | 600/411 |
| 6,128,522 | * 10/2000 | Acker et al. | 600/411 |

* cited by examiner

Primary Examiner—Marvin M. Lateef
Assistant Examiner—Jeoyuh Lin
(74) Attorney, Agent, or Firm—Jean K. Testa; Donald S. Ingraham

(57) ABSTRACT

An MRI system acquires NMR tracking data from a tracking coil imbedded in an ablation device which is guided by a physician using real time anatomic images produced from image data acquired by the MRI system. The same tracking coil is energized by an RF power source to deliver energy which ablates tissue after the device is guided into proper position.

14 Claims, 6 Drawing Sheets

MRI GUIDED ABLATION SYSTEM

BACKGROUND OF THE INVENTION

The field of the invention is nuclear magnetic resonance imaging (MRI) methods and systems. More particularly, the invention relates to the tracking of RF ablation devices using MRI methods.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped",into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles, or "views",in which these gradients vary according to the particular localization method being used. The resulting set of received NMR signals are digitized and processed to reconstruct the image using one of many well known reconstruction techniques.

Intra-operative MR imaging is employed during a medical procedure to assist the doctor in guiding an Instrument. For example, during a needle biopsy the MRI system is operated in a real-time mode in which image frames are produced at a high rate so that the doctor can monitor the location of the needle as it is inserted. A locator device such as that described in U.S. Pat. Nos. 5,622,170 and 5,617,857 may be used to track the location of the instrument and provide coordinate values to the MRI system which enable it to mark the location of the instrument in each reconstructed image. The medical instrument is attached to a handpiece that is manipulated by the physician and whose position is detected by surrounding sensors. For example, the handpiece may emit light from two or more light emitting diodes which is sensed by three stationary cameras.

Tracking devices which employ the MRI system to locate markers in the medical device have also been developed. As described in U.S. Pat. Nos. 5,271,400; 5,307,808; 5,318,025; 5,353,795 and 5,715,822, such tracking systems employ a small coil attached to a catheter or other medical device to be tracked. An MR pulse sequence is performed using the tracking coil to acquire a signal which indicates the location of the tracked device. The location of the tracking coil is determined and is superimposed at the corresponding location in a medical image acquired with the same MRI system.

To accurately locate the tracking coil, position information is obtained in three orthogonal directions that require at least three separate measurement pulse sequences. To correct for errors arising from resonance offset conditions, such as transmitter misadjustment and susceptibility effects, two measurements may be made in each direction with the polarity of the readout gradient reversed in one measurement. This tracking method requires that six separate measurement pulse sequences be performed to acquire the tracking coil location. As disclosed in U.S. Pat. No. 5,353,795, these separate measurements can be reduced to four in number by altering the readout gradients in a Hadamard magnetic resonance tracking sequence.

One of the primary medical procedures which employs intra-operative MR imaging is ablation therapy. As described, for example, in U.S. Pat. Nos. 5,443,489; 5,551,426; 5,697,925; 5,718,701 and 5,800,428, ablation devices are precisely guided into position against target tissue. Radio frequency power is applied to the ablation device and this energy creates electric fields in the tissue. These fields cause electrical currents to flow in the tissue since the tissue is electrically conductive. If the currents are strong enough, heating occurs and the temperature can be high enough to destroy tissue cells. Needless to say, it is important that such ablation devices be accurately positioned and the radio frequency power be precisely controlled to only destroy the target tissues.

SUMMARY OF THE INVENTION

The present invention is an ablation system which employs an ablation device that is guided into position by a physician and then energized with radio frequency power to treat target tissues. More particularly, the system includes: an ablation device that contains a tracking coil; an MRI system which is operable to acquire image data from a patient being treated with the ablation device and being operable to acquire NMR tracking data from the tracking coil; and an ablation control for providing radio frequency power to the tracking coil to treat target tissues. The tracking coil serves dual purposes. It provides NMR tracking data for the MRI system which is used to help the physician guide the ablation device into the proper treatment position, and then it is used by the ablation system to deliver the heat generating energy to the target tissues.

One aspect of the present invention is the use of a tracking coil in an ablation device to provide NMR tracking data to an MRI system and to receive RF power from an ablation system. A switch operated by the MRI system couples the tracking coil to a receiver in the MRI system when it performs a position measurement NMR pulse sequence. The same switch may be used to couple the ablation control to the tracking coil at other times during the procedure, or the ablation control can be inductively coupled to the tracking coil.

DESCRIPTION OF THE PREFERRED EMBODIMENT

Figure 1:
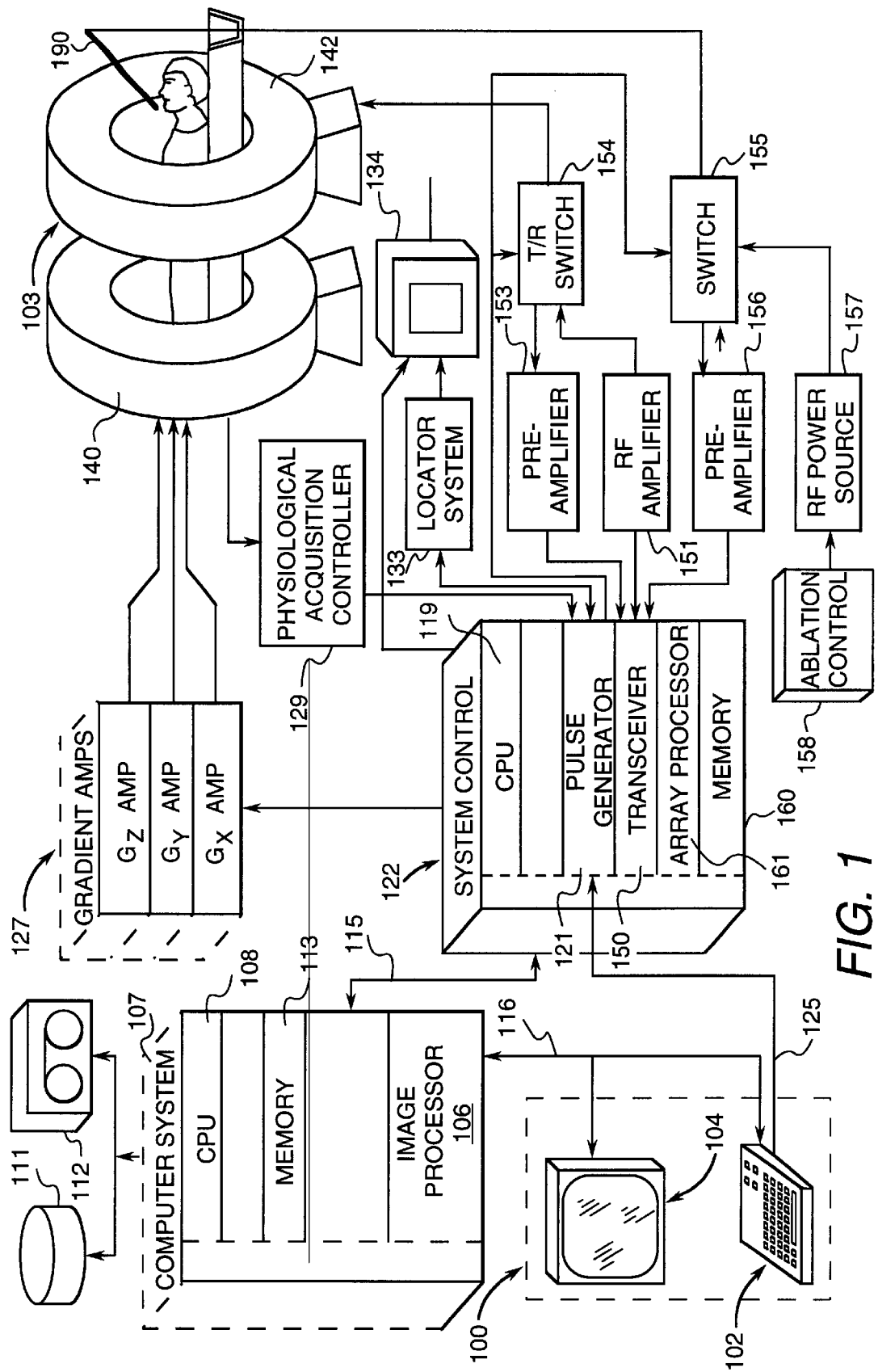
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in a magnet system 103 to produce the magnetic field gradients used for position encoding acquired signals. A transceiver module 150 in the system control 122 produces pulses which are amplified by an RF amplifier 151 and coupled to an RF coil In the magnet assembly 103 by a transmit/receive switch 154. The resulting signals radiated by the excited nuclei in the patient may be sensed by the same RF coil and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the RF coil during the transmit mode and to connect the preamplifier 153 during the receive mode.

Referring still to FIG. 1, the present invention includes an ablation device 190 that is guided by the attending physician into a position in which a patient located in the bore of the magnet system 103 may be treated. As will be described in more detail below, the ablation device 190 includes a tracking coil that serves the dual purposes of acquiring NMR tracking data and applying therapeutic doses of radio frequency energy to target tissues. This tracking coil is connected to an electronic switch 155 that is controlled by a signal from the pulse generator 121 to connect the coil to either the input of a second pre-amplifier 156 or the output of an RF power source 157. As will be described in more detail below, when a tracking coil measurement pulse sequence is performed, the tracking coil is momentarily connected to the preamplifier 156 and an acquired NMR signal is input to the transceiver module 150. Otherwise, the tracking coil remains connected to the RF power source 157.

The RF power source 157 is operated by an ablation control system 158 under directions input by the attending physician. The RF power source 157 produces an oscillating electrical signal at a selected frequency and power. In some embodiments it may be useful to choose a frequency which is outside the sensitive bandwidth of the MR imaging system. In other embodiments, the frequency of the oscillating electrical signal may be within the bandwidth of the MR imaging system and various electrical components such as filters and switches may be employed to prevent the introduction of artifacts in the acquired MR images. In the present invention this oscillating electrical signal is passed onto ablation device 190 for the purpose of creating a strong electric field at the therapeutic portion of the device. The strong electric field induces currents to flow in the surrounding tissue. If the electric field is strong enough, these currents create sufficient heat to destroy tissue. The ablation control system 158 is used by the operator to control the amount of power delivered during the procedure, and temperature feedback may be employed to permit greater operator control of the ablation therapy. This feedback can be provided by temperature-sensitive transducers 204 (shown in FIG. 2, as part of ablative device 190) such as thermocouples and/or fiber-optic sensors incorporated into the ablative device 190 as described, for example, in U.S. Pat. Nos. 5,697,925 and 5,718,701. In alternative embodiments, temperature feedback can also be provided by the Magnetic Resonance Scanner through the use of temperature-sensitive imaging pulse sequence that is interleaved with the tracking pulse sequence.

The NMR signals acquired by an RF coil are digitized by the transceiver module 150 and transferred to a memory module 160 in the system control 122. When an array of k-space image data has been acquired in the memory module 160, an array processor 161 operates to Fourier transform the k-space data into an array of image data which is presented to the attending physician on a display 134. This image data may also be conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

As will be described in more detail below, tracking coil measurement acquisitions are interleaved with the acquisition of image data and NMR tracking data is acquired and Fourier transformed by the array processor 161. The transformed NMR tracking data is used by a locator system 133 to produce an icon representing the medical device for display 134. The icon is overlaid on the NMR image of the patient anatomy at the location indicated by the tracking coil.

While a conventional MRI system may be used to implement the invention, in the preferred embodiment an MRI system which is designed to allow access by a physician is employed. Referring particularly to FIG. 1, when an intraoperative MR imaging procedure is conducted a patient is placed in the magnet system 103 and a region of interest in the patient is aligned near the system isocenter located between the two, spaced magnet rings 140 and 142. A physician standing between magnet rings 140 and 142 has unrestricted access to the region of interest in the patient.

Figure 2:
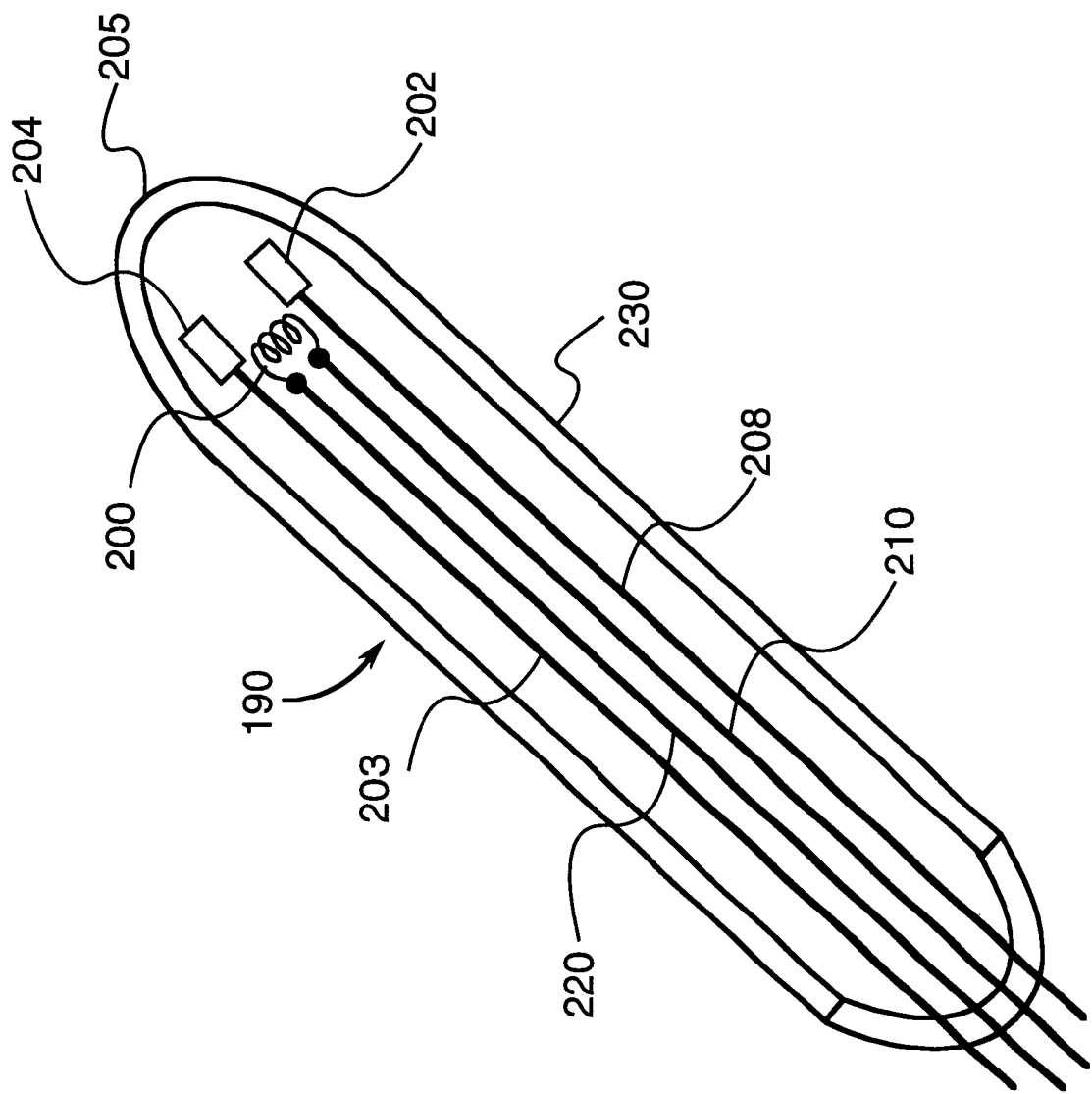
FIG. 2 is a schematic diagram of preferred embodiment of an ablation device.

Referring particularly to FIG. 2, the ablation device 190 designed for insertion into the patient includes a small tracking coil 200 mounted in its operative end 205. The tracking coil 200 has a plurality of turns, and typically may have from 1 to 20 turns. It may be as small as 1 mm in diameter. The ablation device 190 may, for example, be part of a catheter such as that described in U.S. Pat. Nos. 5,271,400 and 5,353,795 or an RF catheter such as that described in U.S. Pat. No. 5,437,277. The tracking coil 200 is small and it has a small region of sensitivity that picks up NMR signals from excited spins only in its immediate vicinity. The acquired NMR signals are conveyed by a pair of conductors 210 and 220 to the switch 155 in the MRI system.

The conductors 210 and 220 are encased along with the tracking coil 200 in an outer shell 230. In the present invention, the conductors 210 and 220 are used to carry the oscillating electrical signals used for ablation. Since the ablation is performed by the creation of high electric fields at the end of the ablative device 190, the oscillating electrical signals can be applied as common mode signals to both conductors 210 and 220.

In an alternative embodiment, dedicated conductors can be incorporated into the ablation device 190 to carry the ablation power. In the embodiment shown in FIG. 2, a single conductor 208 with an electric field shaping tip 202, is used to deliver ablation power. The therapeutic oscillating electrical signals are thus sent by a path independent of the conductors 210 and 220.

Figure 5:
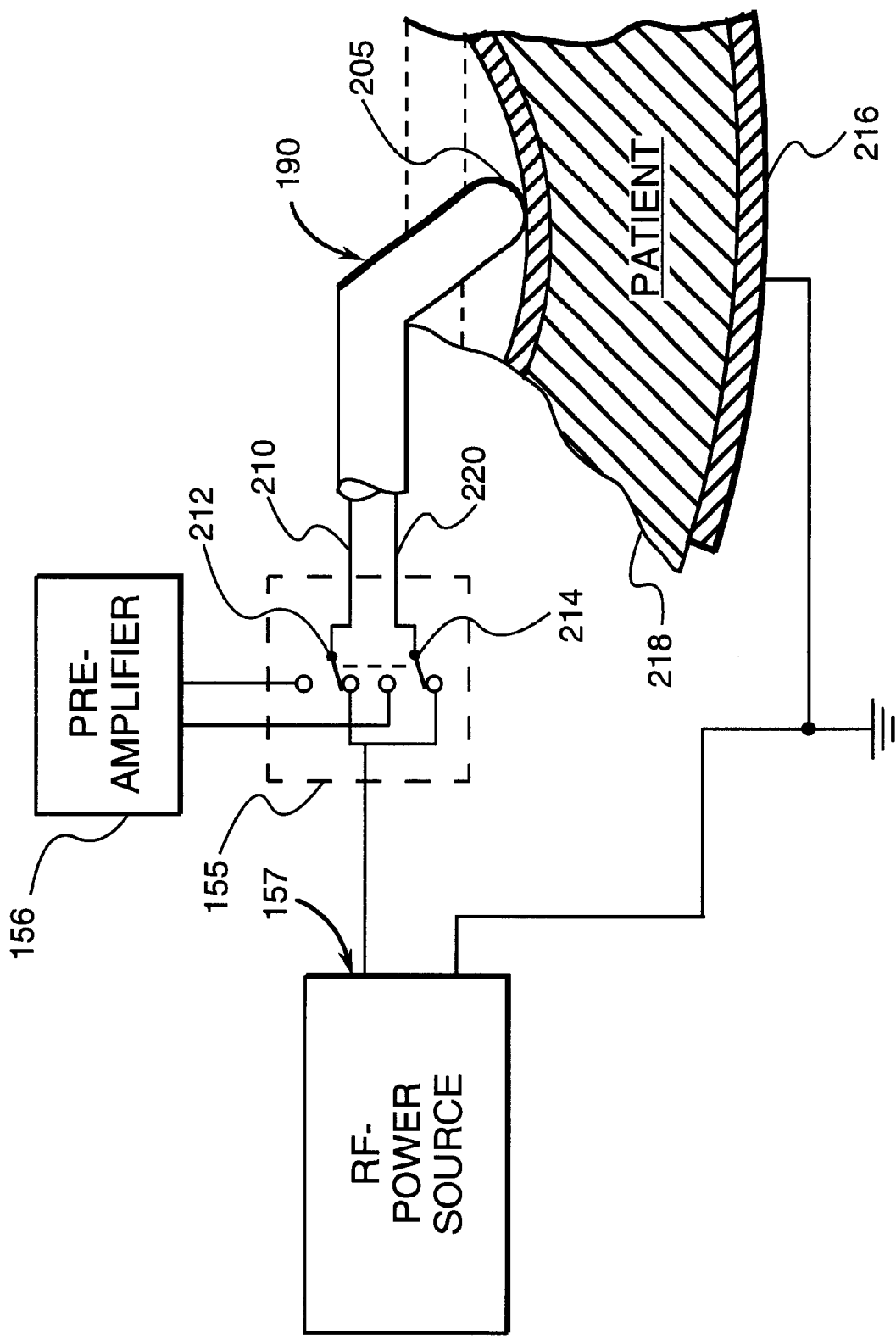
FIG. 5 is a schematic diagram of a preferred embodiment of the connection between the RF power source of FIG. 1 and the ablation device of FIG. 2 in which direct coupling is used.

A direct connection is made between the RF power source 157 and the ablative device 190 as shown in FIG. 5. The two conductive leads 210 and 220 connect to two respective switch poles 212 and 214 in the switch 155. One lead on the RF power source 157 connects to one terminal of each switch pole 212 and 214 and the other terminals connect to the preamplifier 156. The second output terminal on the RF power source 157 is connected to ground and to an electrode 216 attached to the patient 218. As is well known in the art, the electrode 216 is large in area such that the current which flows in tissues between the operating end 205 of the ablation device 190 and the electrode 216 is widely dispersed except in the region which touches the operating end 205. This approach provides excellent transfer efficiency, but requires a physical connector to be incorporated into the ablative device 190.

Figure 6:
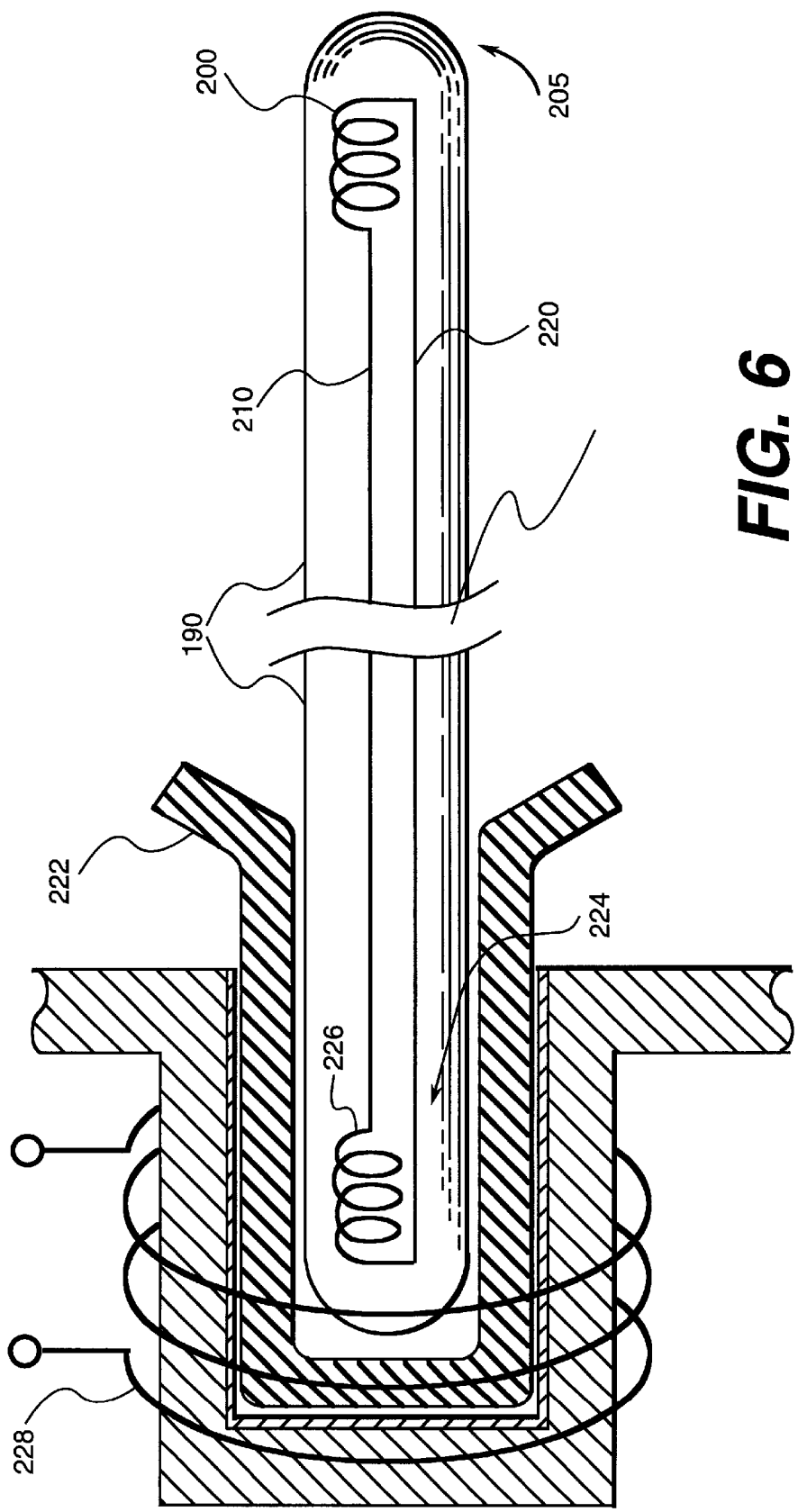
FIG. 6 is a schematic diagram of a second preferred embodiment of the connection between the RF power source of FIG. 1 and the ablation device of FIG. 2 in which inductive coupling is used.

In a second embodiment shown in FIG. 6, inductive coupling is used to connect the RF power source 157 to the ablative device 190. Inductive coupling of the ablative device 190 can be implemented as described in U.S. Pat. No. 5,437,277 which is incorporated herein by reference. A sterile barrier 222 is placed between the RF power source 157 and the nonoperating end 224 of the ablative device 190. The two conductors 210 and 220 are terminated in a coil 226 that is inductively coupled to a surrounding coil 228 on the other side of the sterile barrier 222. The surrounding coil 228 connects to an electronic switch that connects its leads to either the RF power source 157 or the preamplifier 156.

In yet another embodiment, a large transmit coil can be placed around the patient and the ablative power can be inductively coupled to the device in-situ. This large external coil may be the RF transmit coil in the MRI system which is connected to the RF power source 157 through an electric switch that connects the RF coil to either the transceiver module 150 or the RF power source 157.

Figure 3:
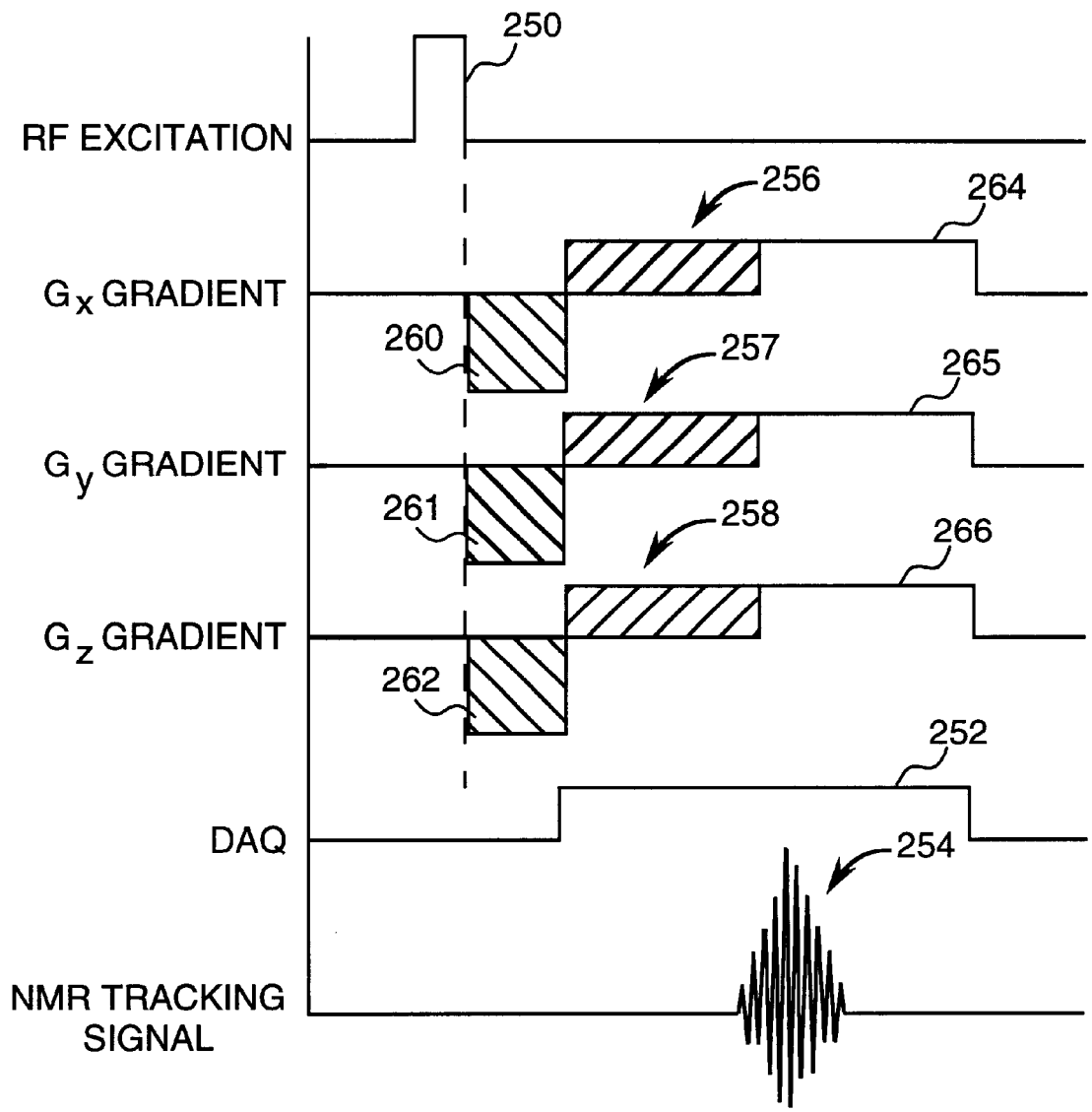
FIG. 3 is a graphic representation of an NMR pulse sequence used by the MRI system of FIG. 1 to measure the position of the tracking coil of FIG. 2.

The position of the tracking coil 200 relative to the gradient iso-center is measured using a position measurement NMR pulse sequence shown in FIG. 3. This gradient recalled echo pulse sequence yields a signal that is essentially a Fourier transform of a projection of the coil location along the readout gradient direction. Assuming that the tracking coil 200 is small, its position $S_1$ is modeled by:

$$S_1 = \frac{\Delta \omega}{\gamma G_1} \Big| \tag{1}$$

where $\Delta\omega$ is the measurement angular frequency of the gradient echo signal relative to $\omega_0$ the Larmor frequency $\gamma$, is the gyromagnetic ratio of the nuclear spins, and $G_1$ is the applied readout gradient. The three-dimensional position of each tracking coil 200 can be identified from three linearly independent gradient echoes.

As described in the above cited U.S. Pat. No. 5,353,795 issued on Oct. 11, 1994 and entitled "Tracking System To Monitor The Position Of A Device Using Multiplexed Magnetic Resonance Detection", which is incorporated herein by reference, errors arising from resonance offset conditions make it necessary to acquire more than three tracking coil measurements. While it is possible to acquire two measurements along each gradient axis to obtain the necessary error free tracking NMR data, such an approach requires six separate measurements. In the preferred embodiment a Hadamard MR tracking sequence is performed using the measurement pulse sequence of FIG. 3. It requires only four separate measurements to acquire a complete NMR tracking coil data set.

Referring particularly to FIG. 3, the tracking coil measurement pulse sequence includes a non-selective RF excitation pulse 250 that is applied to the MRI system whole body RF coil. It has a selected flip angle of from 10 to 60, degrees and it produces transverse magnetization in spins located throughout the magnet bore. Three gradient waveforms 256, 257 and 258 are then applied to produce a gradient recalled NMR echo signal. The switch 155 is controlled during a data acquisition window 252 to receive an NMR tracking signal 254 from the tracking coil 200. The three gradient waveforms 256, 257 and 258 are applied along the respective $G_x$, $G_y$ and $G_z$ gradient axes, and each includes a respective dephase lobe 260, 261 and 262 and a respective readout lobe 264, 265 and 266. As indicated by the cross hatching, the area of each dephasing lobe 260–262 is equal to one-half the area of the respective readout lobes 264–266.

In the measurement pulse sequence of FIG. 3, all of the gradients waveforms 256–258 have the same polarity which is designated herein "+", with waveforms 260–262 having an opposite polarity designated as "−". This pulse sequence is performed a total of four times with the polarity of the $G_x$, $G_y$ and $G_z$ gradient pulses selectively reversed as set forth in Table 1.

TABLE 1

|  | $G_x$ | $G_y$ | $G_z$ |
| --- | --- | --- | --- |
| acquisition 1 | − | − | − |
| acquisition 2 | + | + | − |
| acquisition 3 | + | − | + |
| acquisition 4 | − | + | + |

As indicated above, the four NMR tracking signals 254 are Fourier transformed to produce four corresponding projections $P_1$, $P_2$, $P_3$ and $P_4$. Together, these four projections form an NMR tracking data set from which the x, y and z coordinates of the tracking coil position can be calculated.

A scan according to the preferred embodiment of the invention is carried out by a series of steps depicted in FIG.

4. During this scan, the MRI system acquires image data and reconstructs images of the patient which are produced on the display 134. The MRI system also periodically acquires tracking signals from the tracking coil 200 in the ablation device 190, calculates the position of the tracking coil 200 and overlays an icon of the ablation device on the image being displayed. The physician uses this display to guide the ablation device 190 into the desired position in the patient with its tip in contact with the tissue to be ablated. The physician then operates the ablation control 158 to provide RF power to the tracking coil 200 to ablate the tissue. The steps of moving the ablation device 190 and ablating tissue are repeated as many times as necessary to obtain the desired medical result.

Figure 4:
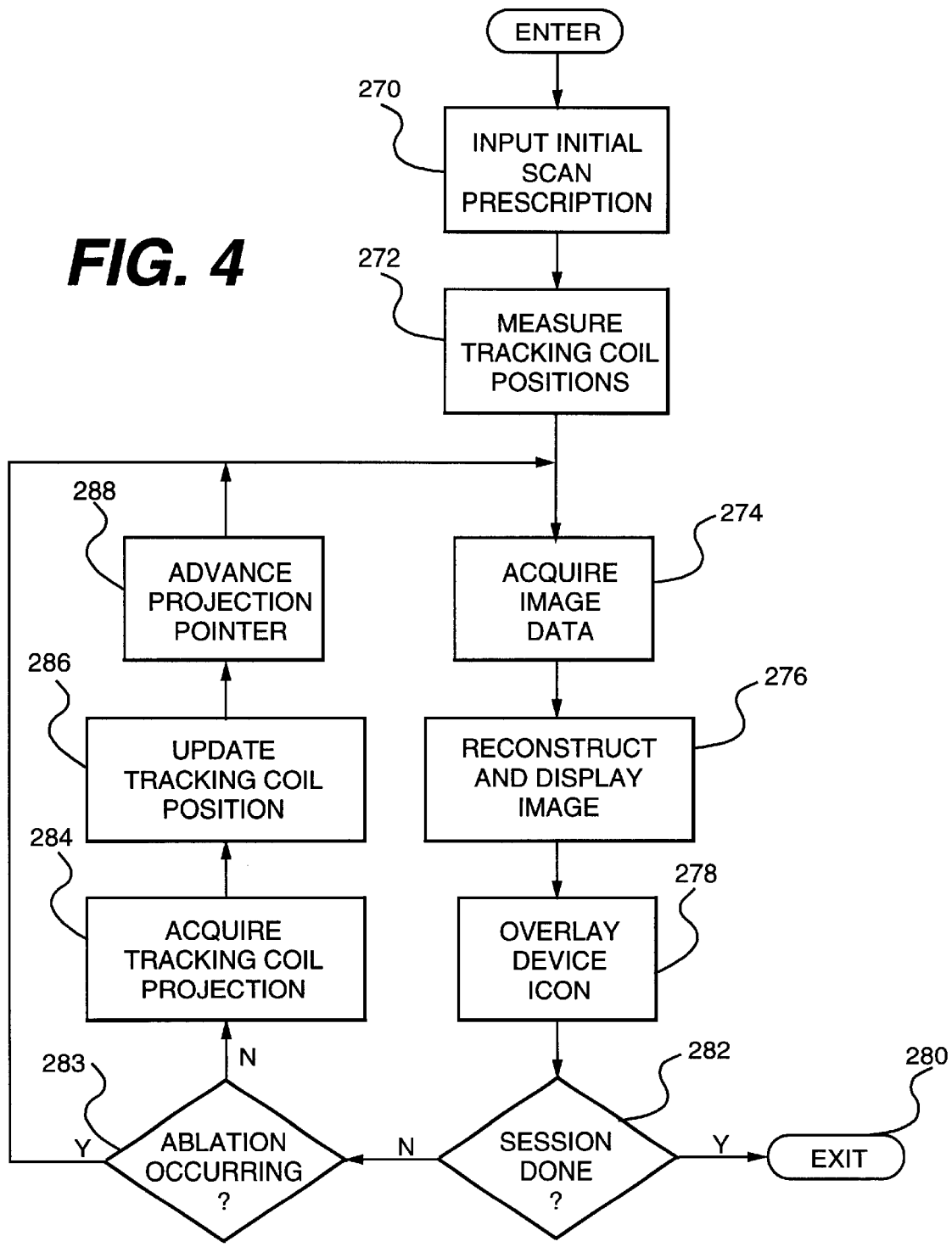
FIG. 4 is a flow chart of the preferred method used to practice the present invention.

Referring particularly to FIG. 4, when the procedure is started the operator enters the initial scan prescription as indicated at process block 270. As indicated above, this includes the selection of an appropriate NMR imaging pulse sequence and the scan parameters that locate and orient the slice plane or 3D volume which is to be imaged.

As indicated by process block 272, the next step is to measure the current position of the tracking coil 200. This is done by acquiring the four projections $P_1-P_4$ as described above with the Hadamard encoding indicated in Table 1. The locations of the signal peaks L1, L2, L3, L4 in each projection P1, P2, P3, P4 are then combined as follows:

$$S_x = -L_1 + L_2 + L_3 - L_4 \qquad (1)$$

$$S_y = -L_1 + L_2 - L_3 + L_4 \qquad (2)$$

$$S_z = -L_1 - L_2 + L_3 - L_4 \qquad (3)$$

to provide the coordinates $S_x$, $S_y$ and $S_z$ of the tracking coil 200.

Referring still to FIG. 4, a loop is entered in which image data is acquired and displayed and the device location is indicated on the display 134. Image data is acquired using the prescribed imaging pulse sequence as indicated at process block 274. As indicated above, this acquired k-space image data is Fourier transformed to reconstruct an image of patient anatomy as indicated at process block 276, and this is output to the display 134 for immediate viewing by the attending physician. The locator system 133 also overlays a device icon on this image as indicated at process block 278 using the previously calculated tracking coil position to locate the icon on the display screen 134.

A number of variations are possible in the image acquisition and reconstruction steps 274 and 276. In some cases a less than complete set of k-space data may be acquired and used to update the image as described, for example, in U.S. Pat. No. 4,830,012. Also, if there is little movement in the patient, or if movement occurs very slowly or only occasionally, it may not be necessary to acquire additional image data to update the anatomical image during each pass. This option is controlled by the physician who can slow or stop the rate of anatomic image updating. The location of the ablation device icon will continue to be updated on the display 134 with the most current tracking coil position data.

If the session is complete, the system exits at 280, otherwise, the system loops back at decision block 282. A check is made at decision block 283 to determine if the tracking coil 200 is currently being used by the physician to ablate tissue. If so, the tracking coil position is not updated. Otherwise, the tracking coil measurement pulse sequence of FIG. 3 is performed once to acquire one of the four tracking coil projections $P_1-P_4$ as indicated at process block 284. Only one projection is acquired and a projection pointer is maintained that indicates which projection is to be acquired during each pass. The newly acquired projection is written over the corresponding outdated projection in the stored NMR tracking data set, and the tracking coil position is updated as indicated at process block 286 using equations (1), (2) and (3) with the newly acquired projection. As indicated at process block 288, the projection pointer is then advanced so that the next projection will be acquired during the next pass. This is done by incrementing the pointer by one until the fourth projection, $P_4$, is acquired and then resetting the pointer to the first projection, $P_1$. The projections $P_1-P_4$ are thus updated one at a time in round-robin order throughout the scan.

The tracking coil 200 is effectively time shared between the MRI system which uses it to locate an ablation device icon on display 134 and the ablation control 158 and 157 which uses it to deliver ablation energy to target tissue. This time sharing is accomplished by controlling the switch 155 such that the tracking coil 200 is connected to the ablation system except during the short intervals when a tracking coil measurement pulse sequence is performed by the pulse generator 121.

Many variations are possible from the preferred embodiment described above. For example, the ablative device 190 could be tracked using methods other than MR tracking. Also, the ablative device could incorporate diagnostic components such as endoscopes and biopsy channels. Alternatively, the ablative device 190 could incorporate additional therapeutic components such as a cryo-therapy channel or access for a cutting tool.

While several presently preferred embodiments of the ablation system have been described in detail herein, many modifications and variations will now become apparent to those skilled in the art. It is, therefore, to be understood that the appended claims are intended to cover all such modifications and variations as fall within the true spirit of the invention.

What is claimed is:

1. An ablation system which comprises:
   a) an ablation device having an operating end for guidance by an operator into a treatment position adjacent target tissues in patient;
   b) a tracking coil mounted in the ablation device near said operating end, said tracking coil being operable to acquire tracking data and to deliver radio frequency current which treats the target tissues;
   c) conductors mounted in the ablation device and coupled to the tracking coil, the conductors extending from the operating end toward a non-operating end of the ablation device;
   d) a Magnetic Resonance Imaging (MRI) system for acquiring image data from the patient being treated and being said MRI system being connected to the conductors for acquiring NMR tracking data from the tracking coil as the ablation device is guided into the treatment position, the MRI system being operable to display an image reconstructed from the acquired image data and the acquired NMR tracking data which depicts the location of the tracking coil in the patient; and
   e) an ablation control having a radio frequency power source which is coupled to the tracking coil to control delivery of radio frequency current which treats the target tissues.

2. The ablation system as recited in claim 1 in which the MRI system includes a transceiver for receiving NMR signals and a switch which is operable when acquiring NMR tracking data to connect the conductors to the transceiver.

3. The ablation system as recited in claim 2 in which the switch operates to connect the radio frequency power source to the tracking coil (200) during treatment of the target tissues.

4. The ablation system as recited in claim 1 in which the radio frequency power source is inductively coupled to the tracking coil.

5. The ablation system as recited in claim 4 in which the radio frequency power source is coupled to an RF coil in the MRI system which inductively couples to the tracking coil.

6. The ablation system as recited in claim 4 in which the conductors connect to a first coil disposed at the non-operating end of the ablation device and the radio frequency power source is connected to a second coil which is inductively coupled with the first coil.

7. The ablation system as recited in claim 1 in which the MRI system provides a temperature-sensitive image used for feedback during tissue ablation.

8. The ablation system as recited in claim 1 in which the ablation device incorporates a temperature transducer used for feedback during tissue ablation.

9. The ablation system as recited in claim 1 in which the conductors are connected to the tracking coil of the ablation device and are used to propagate the radio frequency current used to treat the target tissues.

10. The ablation system as recited in claim 1 further comprising:
   a) an electric field shaping tip incorporated into the ablation device; and
   b) at least one dedicated conductor coupled to the electric field shaping tip and radio frequency power source operating to propagate the radio frequency current to electric field shaping tip to treat the target tissues, with of conductors operating to propagate tracking signals to tracking coil.

11. An ablation system for treating target tissues of a subject during acquisition of image data using a Magnetic Resonance Imaging (MRI) system, said ablation system comprising:
   a) an ablation device for treating said target tissues;
   b) a tracking coil mounted in said ablation device, said tracking coil being operable during imaging with said MRI system to supply tracking data indicating a location of said tracking coil to said MRI system, said MRI system acquiring image data from the subject and acquiring said tracking data from said tracking coil as said ablation device is guided into the treatment position, the MRI system being operable to display an image reconstructed from the acquired image data and to display the location of the tracking coil in the subject from the acquired tracking data; and,
   c) an ablation control coupled to said tracking coil for controlling delivery of a radio frequency current to said ablation device during treatment of said target tissues.

12. The ablation system as recited in claim 11 in which the tracking coil is mounted in an insertion end of the ablation device.

13. The ablation system as recited in claim 11 in which the MRI system provides a temperature-sensitive image.

14. The ablation system as recited in claim 11 further comprising conductors mounted in the ablation device, said conductors being coupled to said tracking coil and being used to propagate the radio frequency current used to treat the target tissues.

\* \* \* \* \*